(12) United States Patent
Lee et al.

(10) Patent No.: US 7,521,130 B2
(45) Date of Patent: Apr. 21, 2009

(54) ORGANIC ELECTROLUMINESCENT DISPLAY DEVICE HAVING SUPERIOR CHARACTERISTICS AT HIGH TEMPERATURE

(75) Inventors: Jun-Yeob Lee, Seongnam-si (KR); Yong-Joong Choi, Yongin-si (KR); Jang-Hyuk Kwon, Suwon-si (KR); Ho-Kyoon Chung, Yongi-si (KR)

(73) Assignee: Samsung Mobile Display Co., Ltd., Suwon-si (KR)

( * ) Notice: Subject to any disclaimer, the term of this patent is extended or adjusted under 35 U.S.C. 154(b) by 196 days.

(21) Appl. No.: 10/828,247

(22) Filed: Apr. 21, 2004

(65) Prior Publication Data
US 2005/0112401 A1 May 26, 2005

(30) Foreign Application Priority Data
Nov. 25, 2003 (KR) .................. 10-2003-0084240

(51) Int. Cl.
*H01L 51/54* (2006.01)
*C09K 11/06* (2006.01)

(52) U.S. Cl. ............... 428/690; 428/917; 313/504; 313/506; 257/40; 257/89; 257/E51.044; 546/4; 546/10

(58) Field of Classification Search ............ None
See application file for complete search history.

(56) References Cited

U.S. PATENT DOCUMENTS

| | | | |
|---|---|---|---|
| 6,392,250 B1 | 5/2002 | Aziz et al. ............... 257/40 |
| 6,392,339 B1 | 5/2002 | Aziz et al. ............... 313/504 |
| 2001/0019782 A1 | 9/2001 | Igarashi et al. .......... 428/690 |
| 2002/0055014 A1* | 5/2002 | Okada et al. ............. 428/690 |
| 2002/0182441 A1 | 12/2002 | Lamansky et al. ........ 428/690 |
| 2003/0040627 A1 | 2/2003 | Fujii ........................ 546/2 |
| 2003/0042848 A1* | 3/2003 | Park et al. ................ 313/503 |
| 2003/0068526 A1* | 4/2003 | Kamatani et al. ......... 428/690 |
| 2003/0072964 A1 | 4/2003 | Kwong et al. |
| 2003/0162299 A1 | 8/2003 | Hsieh et al. .............. 436/84 |
| 2003/0197183 A1 | 10/2003 | Grushin et al. |
| 2004/0094768 A1* | 5/2004 | Yu et al. .................. 257/79 |
| 2005/0234240 A1 | 10/2005 | Stossel et al. ........... 546/4 |

FOREIGN PATENT DOCUMENTS

| | | |
|---|---|---|
| CN | 1413426 A | 4/2003 |
| DE | 10215010 | 10/2003 |
| EP | 1239526 | 9/2002 |
| EP | 1245659 | 10/2002 |
| EP | 1348711 | 10/2003 |
| EP | 1371708 | 12/2003 |
| JP | 2001-247859 | 9/2001 |
| JP | 2002-216975 | 8/2002 |
| JP | 2003-73355 | 3/2003 |
| JP | 2003-151769 | 5/2003 |
| WO | WO 01/41512 | 6/2001 |
| WO | WO 02/064700 | 8/2002 |
| WO | WO 03/063555 | 7/2003 |

OTHER PUBLICATIONS

Communication and Search Report issued in European Patent Application No. 04090194.4 on Oct. 20, 2005.
Office Action issued in Chinese Patent Application No. 2004100458001 on Aug. 15, 2008.

* cited by examiner

*Primary Examiner*—Marie R. Yamnitzky
(74) *Attorney, Agent, or Firm*—Stein, McEwen & Bui, LLP (57) ABSTRACT

An organic electroluminescent display device improves driving characteristics at a high temperature and storage characteristics of the organic electroluminescent display device, and prevents pixel contraction phenomena of the device by providing an organic electroluminescent display device comprising a substrate, a first electrode and a second electrode formed on the substrate, and an organic film layer comprising at least one emitting layer between the first electrode and the second electrode. The emitting layer includes at least one phosphorescent dopant, and the dopant is represented by L3M or L2ML', wherein the M is a transition metal selected from the group consisting of Ir, Pt, Zn and Os, the L and L' are bidendate ligands coordinated with carbon and nitrogen, and at least one of the L and L' has 15 or more carbon atoms in the ligand.

15 Claims, 1 Drawing Sheet

FIG. 1
(PRIOR ART)

FIG. 2

ORGANIC ELECTROLUMINESCENT DISPLAY DEVICE HAVING SUPERIOR CHARACTERISTICS AT HIGH TEMPERATURE

CROSS-REFERENCE TO RELATED APPLICATIONS

This application claims the benefit of Korean Patent Application No. 2003-84240, filed on Nov. 25, 2003, the disclosure of which is hereby incorporated herein by reference in its entirety.

BACKGROUND OF THE INVENTION

1. Field of the Invention

The present invention relates to an organic electroluminescent display device and a method to fabricate the organic electroluminescent display device, more particularly, to an organic electroluminescent display device in which an existing emitting layer is improved to have effective characteristics at high temperature, solve contraction phenomena of pixels and have effective, stable driving characteristics, and a method to fabricate the organic electroluminescent display device.

2. Description of the Related Art

Recently, an organic electroluminescent display device has been proposed as a next generation display device since the organic electroluminescent display device has merits of a thin thickness, a wide viewing angle, light weight, a small size, a fast response speed and lower power consumption compared to a cathode ray tube (CRT) or a liquid crystal display device (LCD). Particularly, the organic electroluminescent display device has an advantage in that it is easily fabricated through a simple fabrication process, since the organic electroluminescent display device is constructed in a simple structure of an anode, an organic layer and a cathode. The organic layer may be formed in various layers according to its functions and generally comprises a hole injection layer, a hole transfer layer, an emitting layer, an electron transport layer, and an electron injection layer.

Figure 1:
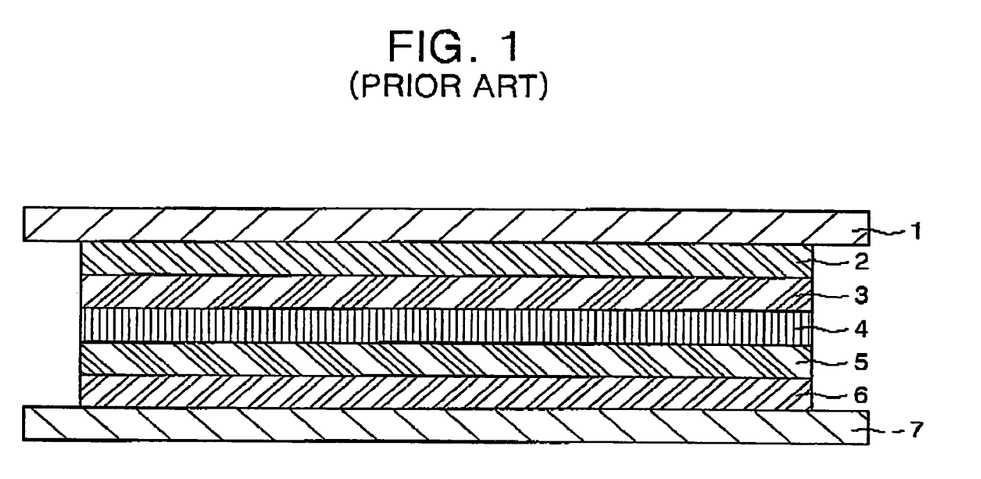
FIG. 1 is a cross sectional view to show, schematically, the structure of a conventional organic electroluminescent display device.

FIG. 1 is a cross sectional view for schematically showing a structure of a conventional organic electroluminescent display device.

Referring to FIG. 1, holes are injected from an anode 7 that is a transparent electrode so that injected holes are transferred to an emitting layer 4 through hole injection layer 6 and hole transfer layer 5, and electrons are injected from a cathode 1 so that the injected electrons are transferred to the emitting layer 4 through the electron injection layer 2 and the electron transfer layer 3. The transferred electrons and the holes combine with each other to emit light. The emitting layer 4 is constructed so that dopant is doped on a host and the electrons and the holes are transferred to the dopant through the host to emit light.

A phosphorescent material, including iridium (Ir) or platinum (Pt), is used as a dopant in the case of a phosphorescent organic electroluminescent display device, while an organic fluorescent material is used as an emitting material in the case of a fluorescent organic electroluminescent display device.

The method of the present invention improves the emitting layer to improve the stability of an organic electroluminescent display device at a high temperature. The life cycle of the organic electroluminescent display device at a high temperature is improved by forming a host of the emitting layer using a mixture of the hole transport layer and the electron transport layer to improve high temperature stability of an organic electroluminescent display device, as is disclosed in U.S. Pat. No. 6,392,339. The stability of the organic electroluminescent display device at a high temperature is improved by suppressing the movement of the holes to the electron transport layer using an emitting layer comprising a mixture of the hole transport layer and the electron transport layer. The driving stability of an organic electroluminescent display device is improved by using a mixture of the hole transport layer and the electron transport layer as a host of the emitting layer and doping a dopant, as is disclosed in U.S. Pat. No. 6,392,250.

However, it has been confirmed that when these methods are applied to a fluorescent material so that the stability of an organic electroluminescent display device is improved at a high temperature, the methods rather reduce the characteristics of the device in the case of a phosphorescent organic electroluminescent display device. Particularly, these methods have a limit in improving characteristics of the device at a high temperature since a host material having electron transportability is limited in the phosphorescent organic electroluminescent display device. Furthermore, it is necessary to improve characteristics of the host of the emitting layer, as well as the characteristics of the dopant, to improve the characteristics of an organic electroluminescent display device.

SUMMARY OF THE INVENTION

Therefore, to solve the foregoing and/or other problems, it is an aspect of the present invention to provide a flat panel display device having an effective stability at high temperature, solving contraction of pixels during driving, and improving stability by improving the emitting layer when forming an organic electroluminescent display device.

To achieve the foregoing and/or other aspects, the present invention provides an organic electroluminescent display device comprising a substrate, a first electrode and a second electrode formed on the substrate, and an organic film layer comprising at least one emitting layer between the first electrode and the second electrode, wherein the emitting layer comprises at least one phosphorescent dopant, and the dopant is represented by L2ML', and wherein the M is one transition metal selected from the group consisting of Ir, Pt, Zn and Os, the L and L' are bidendate ligands coordinated with carbon and nitrogen, and at least one of the L and L' has 15 or more carbon atoms in the ligand.

Furthermore, the present invention provides an organic electroluminescent display device comprising a substrate, a first electrode and a second electrode formed on the substrate, and an organic film layer comprising at least one emitting layer between the first electrode and the second electrode, wherein the emitting layer comprises at least one phosphorescent dopant, and the dopant is represented by L3M, and wherein the M is one transition metal selected from the group consisting of Ir, Pt, Zn and Os, and the L is a bidendate ligand coordinated with carbon, and nitrogen and has 15 or more carbon atoms in the ligand.

Furthermore, the present invention provides an emitting compound characterized in that it is represented by L2ML' or L3M, wherein the M is one transition metal selected from the group consisting of Ir, Pt, Zn and Os, the L and L' are bidendate ligands coordinated with carbon and nitrogen, and at least one of the L and L' has 15 or more carbon atoms in the ligand.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

As described in the above, the present invention uses a dopant having a superior high temperature stability as a dopant doped on a host of an emitting layer device by improving an existing emitting layer material, thus improving the high temperature characteristics and inhibiting the pixel contraction phenomena of an organic electroluminescent display.

Generally, an organometallic complex compound of a metal and a ligand is used as a phosphorescent dopant, transition metals such as Ir, Pt, Zn and Os are used as a metal of the phosphorescent dopant, and an organic compound type ligand is used as the ligand. Generally, a bidendate type ligand and a L2ML' or a L3M type dopant are mainly used in the case of the organic compound ligand.

L and L' are the bidendate ligands, and the M is a transition metal. The structures have superior efficiency and luminance since the triplet state of phosphorescence is used in emission in the foregoing structures. However, the stability at a high temperature and the pixel contraction phenomena of an organic electroluminescent display device are heavily dependent on the structure of a phosphorescent organometallic complex compound.

Coherence between the subsidiary ligand and the metal is weakened at high temperature so that the emission efficiency due to driving is slowly reduced at an ordinary temperature while the emission efficiency is radically reduced at high temperature due to driving since the coherence of the subsidiary ligand of X with metal is small in the case of the L2MX type ligand (where X is a subsidiary ligand such as acetylacetonate).

High temperature characteristics are determined according to the structure of the ligand in the case of a L3M type ligand. High temperature stability of an organic electroluminescent display device is lowered by the deformation of the ligand at high temperature if the ligand has a low glass transition temperature and has a soft structure of less than 15 carbon atoms, while driving of the organic electroluminescent display device at high temperature is stabilized if a ligand has a rigid structure comprising 15 or more of carbon atoms and has a high glass transition temperature.

Also in the case of L2ML', the high temperature stability of the device is determined by the rigidity of ligands of L and L', and the high temperature stability of the device is improved when a rigid structure comprising 15 or more of carbon atoms is used in at least one ligand of L and L'.

Pixel contraction phenomena are caused by oxygen or residual gas existing in the device. Therefore, the pixel contraction phenomena are reduced if a stable dopant is used in the oxygen or residual gas. Therefore, bonding is easily dismantled by the residual gas so that pixel contraction phenomena are shown, since coherence of the subsidiary ligand with the transition metal is weak if the structure of L2MX using a subsidiary ligand is used.

On the contrary, the pixel contraction phenomena are substantially reduced since the L3M and L2ML' are stable in the residual gas in the case of L3M and L2ML' having strong coherence of the transition metal and the ligand.

Therefore, a ligand of phosphorescent dopant to form a transition metal such as Ir, Pt, Zn and Os and an organic complex compound has a structure of L3M or L2ML' to improve a driving stability of an organic electroluminescent display device at high temperature and to reduce the pixel contraction phenomena of the device, and L, a ligand of L3M structure, has 15 or more of carbon atoms in the ligand. It is preferable that at least one of the L and L' has 15 or more of carbon atoms in the ligand in the case of L2ML'.

Figure 2:
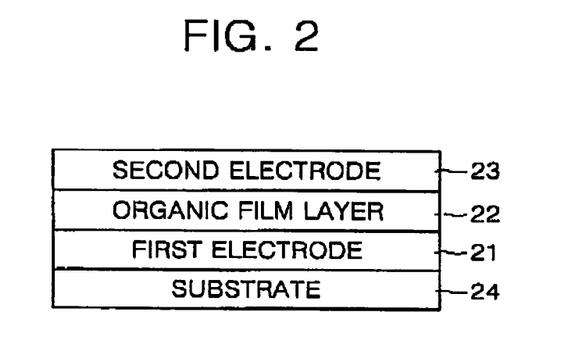
FIG. 2 is a cross-sectional schematic view of one embodiment of an organic electroluminescent display device in accordance with the present invention.

Therefore, as shown in FIG. 2, the present invention provides an organic electroluminescent display device 20 comprising a substrate 24, a first electrode 21 and a second electrode 23 formed on the substrate, and an organic film layer 22 comprising at least one emitting layer between the first electrode 21 and second electrode 23, wherein the emitting layer comprises at least one phosphorescent dopant, and the dopant is represented by L2ML' or L3M.

The M is one transition metal selected from the group consisting of Ir, Pt, Zn and Os, the L and L' are bidendate ligands coordinated with carbon and nitrogen, and at least one of the L and L' has 15 or more carbon atoms in the ligand.

It is preferable that at least one of the L and L' has at least two hexagonal ring structures in the ligand.

On the other hand, the L and L' are any one ligand selected from ligands represented by the following chemical formulas 1 to 15 in case of the dopant L2ML':

Chemical Formula 1

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Furthermore, a preferable compound of the L2ML' is any one dopant selected from dopants represented by the following chemical formulas 16 to 22:

Chemical Formula 16

Chemical Formula 17

Chemical Formula 18

Chemical Formula 19

Chemical Formula 20

Chemical Formula 21

-continued

Chemical Formula 22

Chemical Formula 25

The ligand represented by L comprises 15 or more carbon atoms, and a ligand represented by L' may comprise 15 or less carbon atoms in the dopants represented by the above chemical formulas 16 to 22 as well as 15 or more carbon atoms.

In the case of the dopant L3M, the L is any one ligand selected from ligands represented by the formulas 1 to 14 recited above.

Furthermore, a preferable compound of the L3M is any one dopant selected from dopants represented by the following chemical formulas 23 to 31:

Chemical Formula 26

Chemical Formula 23

Chemical Formula 27

Chemical Formula 28

Chemical Formula 24

Chemical Formula 29

-continued

Chemical Formula 30

Chemical Formula 31

The dopants represented by the above chemical formulas 23 to 31 comprise a material having 15 or more carbon atoms contained in L.

On the other hand, the emitting layer comprises subsidiary pixels of a red emitting layer, a green emitting layer and a blue emitting layer, and the blue emitting layer in the emitting layer may comprise a fluorescent emitting layer.

Furthermore, an organic electroluminescent display device comprises a phosphorescent emitting layer using a phosphorescent dopant as the blue emitting layer, and any one of the L and L' comprises a dopant having less than 15 carbon atoms in the ligand in the phosphorescent dopant comprising the phosphorescent emitting layer as the blue emitting layer.

On the other hand, the organic film layer further comprises one or more layers selected from a hole injection layer, a hole transport layer, an electron transport layer, an electron injection layer and a hole blocking layer. Particularly, it is preferable that the hole blocking layer is formed between the electron transport layer and the emitting layer, since holes through the emitting layer from the hole transport layer are trapped in the emitting layer. Therefore, the hole blocking layer comprises a common layer over the front surface of a substrate in the case that subsidiary pixels of red, green and blue emitting layers respectively comprise the phosphorescent emitting layer. On the other hand, the hole blocking layer is not formed on an upper part of the blue emitting layer, or the blue emitting layer is formed as a common layer on an upper part of phosphorescent red and green emitting layers in the case that the blue emitting layer in the emitting layer comprises a fluorescent emitting layer.

On the other hand, the second electrode is a cathode electrode if the first electrode is an anode electrode, the second electrode is an anode electrode if the first electrode is a cathode electrode, and the other electrode comprises a transparent electrode if any one electrode of the first electrode or the second electrode comprises a reflection electrode.

As described in the above, an organic electroluminescent display device may be fabricated in which stability is greatly improved at high temperature, and the pixel contraction phenomena are reduced by using a phosphorescent dopant having a structure of the present invention compared to a structure in which an existing ordinary phosphorescent dopant is doped on a host.

Preferable examples of the present invention are suggested as follows. However, the following examples are suggested only to help understand the present invention, but the present invention is not limited to the following examples.

EXAMPLE 1

A hole transport layer of N,N'-di(1-naphtyl)-N,N'-diphenylbenzidine (NPD) was deposited on the hole injection layer to a thickness of 50 nm under the vacuum of $10^{-6}$ torr after depositing copper phthalocyanine (CuPc) as a hole injection layer of an organic electroluminescent display device to a thickness of 10 nm on an ITO transparent electrode under the vacuum of $10^{-6}$ torr. An emitting layer was formed to a thickness of 30 nm on the hole transport layer by depositing tris (1-phenylquinoline)iridium of the following chemical formula 27 to a concentration of 10% on carbazole biphenyl (CBP) after depositing NPD on the copper phthalocyanine (CuPc). An electron transport layer of tris(8-quinolinolato) aluminum (Alq) was deposited to a thickness of 20 nm on the hole blocking layer under the vacuum of $10^{-6}$ torr after depositing a hole blocking layer of biphenoxy-bi(8-quinolinolato) aluminum (BAlq) to a thickness of 5 nm on the emitting layer. An electron injection layer of LiF was deposited to a thickness of 1 nm on the electron transport layer after depositing the electron transport layer on the hole blocking layer. The metal electrode deposited LiF electron injection layer was sealed using a metal can and barium oxide (BaO) after finally depositing Al as a metal electrode to a thickness of 300 nm on the LiF electron injection layer.

Chemical Formula 27

An organic electroluminescent display device fabricated using the foregoing processes showed a luminance of 300 cd/m$^2$, an emission efficiency of 8.0 cd/A and color coordinates of 0.62 and 0.37 at 6 V. The life cycle of the organic electroluminescent display device was 3,500 hours at a temperature of 70° C., and an emission efficiency of 800 cd/m$^2$ was a life cycle evaluation result of the organic electroluminescent display device at a high temperature of 70° C. Pixel contraction phenomena were not observed during the driving of the organic electroluminescent display device.

EXAMPLE 2

A hole transport layer of N,N'-di(1-naphtyl)-N,N'-diphenylbenzidine (NPD) was deposited on the hole injection layer to a thickness of 50 nm under the vacuum of $10^{-6}$ torr after depositing copper phthalocyanine (CuPc) as a hole injection layer of an organic electroluminescent display device to a thickness of 10 nm on an ITO transparent electrode under the vacuum of $10^{-6}$ torr. An emitting layer was formed to a thickness of 30 nm on the hole transport layer by depositing tris (1-phenylquinoline) iridium of the following chemical formula 28 to a concentration of 10% on carbazole biphenyl (CBP) after depositing NPD on the copper phthalocyanine (CuPc). An electron transport layer of tris(8-quinolinolato) aluminum (Alq) was deposited to a thickness of 20 nm on the hole blocking layer under the vacuum of $10^{-6}$ torr after depositing a hole blocking layer of biphenoxy-bi(8-quinolinolato) aluminum (BAlq) to a thickness of 5 nm on the emitting layer. An electron injection layer of LiF was deposited to a thickness of 1 nm on the electron transport layer after depositing the electron transport layer on the hole blocking layer. The metal electrode deposited LiF electron injection layer was sealed using a metal can and barium oxide (BaO), after finally depositing Al as a metal electrode to a thickness of 300 nm on the LiF electron injection layer.

Chemical Formula 28

An organic electroluminescent display device fabricated using the foregoing processes showed a luminance of 230 cd/m², an emission efficiency of 5.0 cd/A and color coordinates of 0.67 and 0.32 at 6 V. The life cycle of the organic electroluminescent display device was 4,000 hours at temperature of 70° C., and an emission efficiency of 800 cd/m² was a life cycle evaluation result of the organic electroluminescent display device at high temperature of 70° C. Pixel contraction phenomena were not observed during the driving of the organic electroluminescent display device.

COMPARATIVE EXAMPLE 1

A hole transport layer of N,N'-di(1-naphtyl)-N,N'-diphenylbenzidine (NPD) was deposited on the hole injection layer to a thickness of 50 nm under the vacuum of $10^{-6}$ torr after depositing copper phthalocyanine (CuPc) as a hole injection layer of an organic electroluminescent display device to a thickness of 10 nm on an ITO transparent electrode under the vacuum of $10^{-6}$ torr. An emitting layer was formed to a thickness of 30 nm on the hole transport layer by depositing bis (1-phenylisoquinoline) iridium acetylacetate to a concentration of 10% on carbazole biphenyl (CBP) after depositing NPD on the copper phthalocyanine (CuPc). An electron transport layer of tris(8-quinolinolato)aluminum (Alq) was deposited to a thickness of 20 nm on the hole blocking layer under the vacuum of $10^{-6}$ torr after depositing a hole blocking layer of biphenoxy-bi(8-quinolinolato)aluminum (BAlq) to a thickness of 5 nm on the emitting layer. An electron injection layer of LiF was deposited to a thickness of 1 nm on the electron transport layer after depositing the electron transport layer on the hole blocking layer. The metal electrode deposited LiF electron injection layer was sealed using a metal can and barium oxide (BaO), after finally depositing Al as a metal electrode to a thickness of 300 nm on the LiF electron injection layer.

An organic electroluminescent display device fabricated using the foregoing processes showed a luminance of 300 cd/m², an emission efficiency of 11.0 cd/A and color coordinates of 0.62 and 0.37 at 6 V. The life cycle of the organic electroluminescent display device was 1,000 hours at a temperature of 70° C., and an emission efficiency of 800 cd/m² was a life cycle evaluation result of the organic electroluminescent display device at a high temperature of 70° C. Pixel contraction phenomena began to appear after 100 hours, since the organic electroluminescent display device was driven.

COMPARATIVE EXAMPLE 2

A hole transport layer of N,N'-di(1-naphtyl)-N,N'-diphenylbenzidine (NPD) was deposited on the hole injection layer to a thickness of 50 nm under the vacuum of $10^{-6}$ torr after depositing copper phthalocyanine (CuPc) as a hole injection layer of an organic electroluminescent display device to a thickness of 10 nm on an ITO transparent electrode under the vacuum of $10^{-6}$ torr. An emitting layer was formed to a thickness of 30 nm on the hole transport layer by depositing bis (1-phenylisoquinoline) iridium tetramethylheptanedione to a concentration of 10% on carbazole biphenyl (CBP) after depositing NPD on the copper phthalocyanine (CuPc). An electron transport layer of tris(8-quinolinolato)aluminum (Alq) was deposited to a thickness of 20 nm on the hole blocking layer under the vacuum of $10^{-6}$ torr after depositing a hole blocking layer of biphenoxy-bi(8-quinolinolato)aluminum (BAlq) to a thickness of 5 nm on the emitting layer. An electron injection layer of LiF was deposited to a thickness of 1 nm on the electron transport layer after depositing the electron transport layer on the hole blocking layer. The metal electrode deposited LiF electron injection layer was sealed using a metal can and barium oxide (BaO), after finally depositing Al as a metal electrode to a thickness of 300 nm on the LiF electron injection layer.

An organic electroluminescent display device fabricated using the foregoing processes showed a luminance of 280 cd/m², an emission efficiency of 10.0 cd/A, and color coordinates of 0.62 and 0.37 at 6 V. The life cycle of the organic electroluminescent display device was 500 hours at a temperature of 70° C., and an emission efficiency of 800 cd/m² was a life cycle evaluation result of the organic electroluminescent display device at a high temperature of 70° C. Pixel contraction phenomena began to appear after 30 hours since the organic electroluminescent display device was driven.

COMPARATIVE EXAMPLE 3

A hole transport layer of N,N'-di(1-naphtyl)-N,N'-diphenylbenzidine (NPD) was deposited on the hole injection layer to a thickness of 50 nm under the vacuum of $10^{-6}$ torr after depositing copper phthalocyanine (CuPc) as a hole injection layer of an organic electroluminescent display device to a thickness of 10 nm on an ITO transparent electrode under the vacuum of $10^{-6}$ torr. An emitting layer was formed to a thickness of 30 nm on the hole transport layer by depositing tris (1-phenylpyridine) iridium to a concentration of 5% on carbazole biphenyl (CBP) after depositing NPD on the copper phthalocyanine (CuPc). An electron transport layer of tris(8-quinolinolato)aluminum (Alq) was deposited to a thickness of 20 nm on the hole blocking layer under the vacuum of $10^{-6}$ torr after depositing a hole blocking layer of biphenoxy-bi(8-quinolinolato)aluminum (BAlq) to a thickness of 5 nm on the emitting layer. An electron injection layer of LiF was deposited to a thickness of 1 nm on the electron transport layer after depositing the electron transport layer on the hole blocking layer. The metal electrode deposited LiF electron injection layer was sealed using a metal can and barium oxide (BaO), after finally depositing Al as a metal electrode to a thickness of 300 nm on the LiF electron injection layer.

An organic electroluminescent display device fabricated using the foregoing processes showed a luminance of 250 cd/M$^2$, an emission efficiency of 24.0 cd/A, and color coordinates of 0.29 and 0.62 at 6 V. The life cycle of the organic electroluminescent display device was 700 hours at a temperature of 70° C., and an emission efficiency of 800 cd/M$^2$ was a life cycle evaluation result of the organic electroluminescent display device at a high temperature of 70° C. Pixel contraction phenomena began to appear after 100 hours since the organic electroluminescent display device was driven.

As shown in the foregoing results of the comparative examples, an organic electroluminescent display device of the present invention secures a driving stability at a high temperature and suppresses pixel cotraction phenomena during driving by using a phosphorescent dopant comprising 15 or more carbon atoms in ligands having L3M and L2ML' structures containing iridium (Ir).

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. An organic electroluminescent display device comprising:
   a substrate;
   a first electrode and a second electrode formed on the substrate; and
   an organic film layer comprising at least one emitting layer between the first electrode and the second electrode,
   wherein the emitting layer comprises at least one phosphorescent dopant represented by L3M wherein M is a transition metal selected from the group consisting of Ir and Os, and L is a bidentate ligand coordinated with carbon and nitrogen and is represented by the following chemical formula 14:

Chemical Formula 14

2. The organic electroluminescent display device according to claim 1, wherein the emitting layer comprises a red emitting layer, a green emitting layer and a blue emitting layer to generate red, green and blue colors, respectively, using subsidiary pixels.

3. The organic electroluminescent display device according to claim 2, wherein the blue emitting layer is a blue fluorescent emitting layer.

4. The organic electroluminescent display device according to claim 3, wherein the red emitting layer and the green emitting layer are phosphorescent emitting layers and wherein the blue fluorescent emitting layer is formed on an upper part of the red and green phosphorescent emitting layers over a front surface of the substrate as a common layer.

5. The organic electroluminescent display device according to claim 1, wherein the organic film layer further comprises at least one layer selected from a hole injection layer, a hole transport layer, an electron transport layer, an electron injection layer and a hole blocking layer.

6. The organic electroluminescent display device according to claim 5, wherein the organic film layer comprises a red emitting layer, a green emitting layer and a blue fluorescent emitting layer, and wherein the hole blocking layer is formed on an upper part of the red emitting layer and the green emitting layer.

7. The organic electroluminescent display device according to claim 1, wherein the second electrode is a cathode electrode if the first electrode is an anode electrode, and the second electrode is an anode electrode if the first electrode is a cathode electrode.

8. An organic electroluminescent display device comprising:
   a substrate;
   a first electrode and a second electrode formed on the substrate; and
   an organic film layer comprising at least one emitting layer between the first electrode and the second electrode,
   wherein the emitting layer comprises at least one phosphorescent dopant represented by L2ML' wherein M is a transition metal selected from the group consisting of Ir and Os, the L and L' are bidentate ligands coordinated with carbon and nitrogen, and at least one of the L and L' is represented by the following chemical formula 14:

Chemical Formula 14

9. The organic electroluminescent display device according to claim 8, wherein the emitting layer comprises subsidiary pixels of a red emitting layer, a green emitting layer and a blue emitting layer.

10. The organic electroluminescent display device according to claim 9, wherein the blue emitting layer is a blue fluorescent emitting layer.

11. The organic electroluminescent display device according to claim 10, wherein the red emitting layer and the green emitting layer are phosphorescent emitting layers and wherein the blue fluorescent emitting layer is formed on an upper part of the red and green phosphorescent emitting layers over a front surface of the substrate as a common layer.

12. The organic electroluminescent display device according to claim 8, wherein the organic film layer further comprises at least one layer selected from a hole injection layer, a hole transport layer, an electron transport layer, an electron injection layer and a hole blocking layer.

13. The organic electroluminescent display device according to claim 12, wherein the organic film layer comprises a red emitting layer, a green emitting layer and a blue fluorescent emitting layer, and wherein the hole blocking layer is formed on an upper part of the red emitting layer and the green emitting layer.

14. The organic electroluminescent display device according to claim 8, wherein the second electrode is a cathode electrode if the first electrode is an anode electrode, and the second electrode is an anode electrode if the first electrode is a cathode electrode.

15. An emitting compound having a chemical structure of L2ML' or L3M, wherein the M is a transition metal selected from the group consisting of Ir and Os, the L and L' are bidentate ligands coordinated with carbon and nitrogen, wherein in L2ML', at least one of the L and L' is represented by the following chemical formula 14, and in L3M, L is represented by the following chemical formula 14:

Chemical Formula 14

* * * * *